United States Patent [19]

James, Jr. et al.

[11] Patent Number: 5,068,484

[45] Date of Patent: Nov. 26, 1991

[54] PROCESS FOR THE HYDROCONVERSION OF A FEEDSTOCK COMPRISING ORGANIC COMPOUNDS HAVING A TENDENCY TO READILY FORM POLYMER COMPOUNDS

[75] Inventors: Robert B. James, Jr., Northbrook; Tom N. Kalnes, La Grange, both of Ill.

[73] Assignee: UOP, Des Plaines, Ill.

[21] Appl. No.: 430,394

[22] Filed: Nov. 2, 1989

[51] Int. Cl.$^5$ .................... C07C 1/20; C07C 1/00
[52] U.S. Cl. .................... 585/469; 585/641; 585/733
[58] Field of Search .................... 585/469, 641, 733

[56] References Cited

U.S. PATENT DOCUMENTS

| | | | |
|---|---|---|---|
| 2,328,707 | 9/1943 | Clar et al. | 585/641 |
| 2,504,919 | 4/1950 | Bordner | 585/641 |
| 2,529,590 | 11/1950 | Bloch | 585/641 |
| 2,744,940 | 5/1956 | Pines | 585/733 |
| 2,886,605 | 5/1959 | McClure et al. | 585/733 |
| 3,133,013 | 5/1964 | Watkins | 208/210 |
| 3,592,864 | 7/1971 | Gewartowski | 260/667 |
| 3,595,931 | 7/1971 | Hay | 585/469 |
| 4,740,646 | 4/1988 | Henekis et al. | 585/469 |
| 4,747,937 | 5/1988 | Hillman et al. | 585/469 |
| 4,818,368 | 4/1989 | Kalnes et al. | 585/469 |
| 4,895,995 | 1/1990 | James, Jr. et al. | 585/733 |
| 4,899,001 | 2/1990 | Kalnes et al. | 585/733 |
| 4,902,842 | 2/1990 | Kalnes et al. | 585/733 |

Primary Examiner—Helane E. Myers
Attorney, Agent, or Firm—Thomas K. McBride; John G. Tolomei; John G. Cutts, Jr.

[57] ABSTRACT

A process for the production of a hydrogenated hydrocarbonaceous product from a feedstock comprising organic compounds having a tendency to readily form polymer compounds by means of contacting the feed with a hydrogenated recycle liquid containing dissolved hydrogen in a first hydrogenation reaction zone operated at hydrogenation conditions selected to minimize a hydrogen-rich gaseous phase and to selectively hydrogenate organic compounds having a tendency to readily form polymer compounds and to produce a first hydrogenated stream comprising hydrocarbonaceous compounds and having a reduced concentration of polymer precursors. The resulting first hydrogenated stream is then contacted in a second hydrogenation zone with added hydrogen to produce hydrogenated stream comprising hydrogenated hydrocarbonaceous compounds.

33 Claims, 1 Drawing Sheet

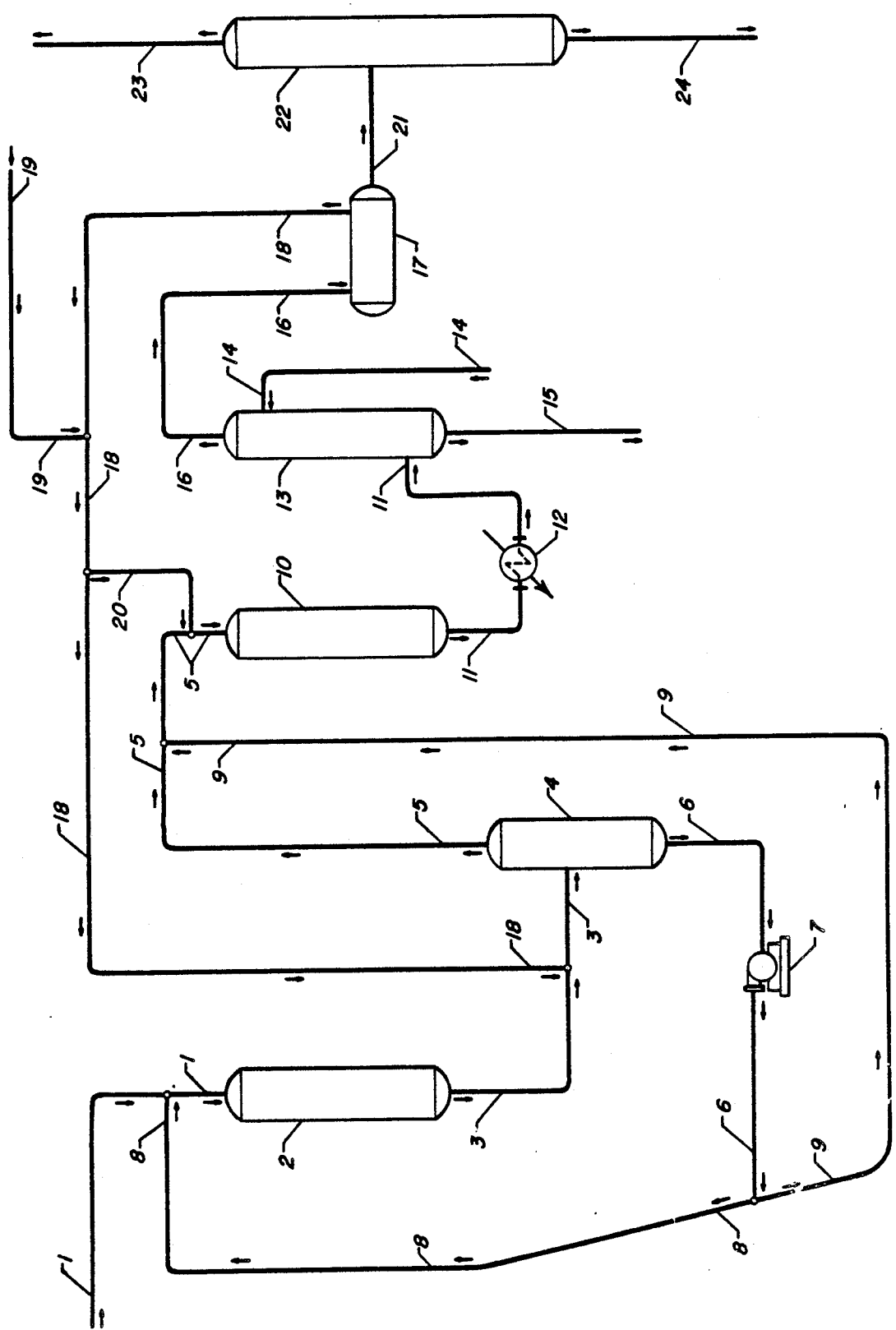

PROCESS FOR THE HYDROCONVERSION OF A FEEDSTOCK COMPRISING ORGANIC COMPOUNDS HAVING A TENDENCY TO READILY FORM POLYMER COMPOUNDS

BACKGROUND OF THE INVENTION

The field of art to which this invention pertains is the production of a hydrogenated hydrocarbonaceous product from a feedstock comprising organic compounds and which feedstock has a tendency to readily form polymer compounds.

More specifically, the invention relates to a process for the hydroconversion of a feedstock comprising organic compounds which are polymer precursors and which process comprises: (a) contacting the feedstock with a hydrogenated recycle liquid containing dissolved hydrogen in a first hydrogenation reaction zone operated at hydrogenation conditions selected to minimize a hydrogen-rich gaseous phase and to selectively hydrogenate the feedstock comprising organic compounds and to produce a first hydrogenated stream comprising hydrocarbonaceous compounds and having a reduced tendency to produce polymers; (b) contacting at least a portion of the first hydrogenated stream with a hydrogen-rich gaseous stream in a saturation zone to produce a second hydrogenated stream containing dissolved hydrogen; (c) introducing at least a portion of the second hydrogenated stream containing dissolved hydrogen into the first hydrogenation reaction zone in step (a) as at least a portion of the hydrogenation recycle liquid; (d) contacting at least another portion of the second hydrogenated stream containing dissolved hydrogen with added hydrogen in a second hydrogenation reaction zone operated at hydrogenation conditions selected to produce a third hydrogenated stream comprising hydrogenated hydrocarbonaceous compounds and hydrogen; and (e) recovering the third hydrogenated stream.

There is a steadily increasing demand for technology which is capable of the hydroconversion of a feedstock comprising organic compounds and which feedstock has a tendency to readily form polymer compounds. Such feedstocks readily polymerize particularly when subjected to conventional hydroconversion. Previous techniques utilized to dispose of such feedstocks which are often undesirable by-products of other manufacturing processes such as vinyl chloride, epichlorohydrin, carbon tetrachloride, styrene and perchloroethylene, for example, have frequently become environmentally unpopular or illegal and, in general, have always been expensive. With the increased environmental emphasis for the treatment and recycle of organic products including chlorinated products, there is an increased need for the conversion of these products in the event that they become unwanted or undesirable. For example, during the disposal or recycle of potentially environmentally harmful diolefinic halogenated organic waste streams, an important step in the total solution to the problem is the conditioning of the diolefinic halogenated organic stream which facilitates the ultimate resolution to provide product streams which may be handled in an environmentally acceptable manner. Therefore, those skilled in the art have sought to find feasible techniques to hydroconvert feedstocks comprising organic compounds which have a tendency to readily form polymer compounds to provide hydrocarbonaceous product streams which may be safely and usefully employed or used. Previous techniques which have been employed include incineration which in addition to potential pollution considerations fails to recover valuable hydrocarbonaceous materials.

INFORMATION DISCLOSURE

In U.S. Pat. No. 3,592,864 (Gewartowski), a process is disclosed for hydrogenating benzene to form cyclohexane utilizing once-through hydrogen-containing gas wherein the exothermic heat of reaction is utilized as the sole source of heat input to steam generation means and wherein the processing system is enhanced by the elimination of recycle gas compressors, treaters, coolers and heaters.

In U.S. Pat. No. 3,133,013 (Watkins), a process is disclosed which relates to the hydrorefining of hydrocarbons for the purpose of removing diverse contaminants therefrom and/or reacting such hydrocarbons to improve the chemical and physical characteristics thereof. In addition, the process is directed toward the selective hydrogenation of unsaturated, coke-forming hydrocarbons through the use of particular conditions whereby the formation of coke, otherwise resulting from the hydrorefining of such hydrocarbon fractions and distillates, is effectively inhibited.

BRIEF SUMMARY OF THE INVENTION

The invention provides an improved process for the production of a hydrogenated hydrocarbonaceous product from a feedstock comprising organic compounds having a tendency to readily form polymer compounds by means of contacting the feed with a hydrogenated recycle liquid containing dissolved hydrogen in a first hydrogenation reaction zone operated at hydrogenation conditions selected to minimize a hydrogen-rich gaseous phase and to selectively hydrogenate organic compounds having a tendency to readily form polymer compounds, and to produce a first hydrogenated stream comprising hydrocarbonaceous compounds and having a reduced concentration of polymer precursors. This resulting first hydrogenated stream is then contacted in a second hydrogenation zone with added hydrogen to produce a hydrogenated stream comprising hydrogenated hydrocarbonaceous compounds and in one preferred embodiment to generate at least one water-soluble hydrogen halide compound. The present invention in one embodiment provides a convenient and economical method for the conversion of by-product or waste organic streams which contain diolefinic, halogenated organic compounds and the recovery of the water-soluble hydrogen halide compound(s) which are produced in the hydrogenation reaction zone. One essential element of the present invention is the controlled hydrogenation of the polymer precursor organic compounds while simultaneously suppressing the high or total hydroconversion of the feedstock thereby preventing the formation of polymers which ensures long continuous runs and lower maintenance costs. Other important elements of the process are the integrated hydrogenation reaction zones which reduce capital and utility costs and in one preferred embodiment the production of hydrogen halide and a hydrocarbonaceous product containing a low concentration of organic halide compounds.

One embodiment of the present invention may be characterized as a process for the hydroconversion of a feedstock comprising organic compounds which are polymer precursors and which process comprises: (a) contacting the feedstock with a hydrogenated recycle liquid containing dissolved hydrogen in a first hydrogenation reaction zone operated at hydrogenation conditions selected to minimize a hydrogen-rich gaseous phase and to selectively hydrogenate the feedstock comprising organic compounds and to produce a first hydrogenated stream comprising hydrocarbonaceous compounds and having a reduced tendency to produce polymers; (b) contacting at least a portion of the first hydrogenated stream with a hydrogen-rich gaseous stream in a saturation zone to produce a second hydrogenated stream containing dissolved hydrogen; (c) introducing at least a portion of the second hydrogenated stream containing dissolved hydrogen into the first hydrogenation reaction zone in step (a) as at least a portion of the hydrogenation recycle liquid; (d) contacting at least another portion of the second hydrogenated stream containing dissolved hydrogen with added hydrogen in a second hydrogenation reaction zone operated at hydrogenation conditions selected to produce a third hydrogenated stream comprising hydrogenated hydrocarbonaceous compounds and hydrogen; and (e) recovering the third hydrogenated stream.

Another embodiment of the invention may be characterized as a process for the hydroconversion of a feedstock comprising organic compounds which are polymer precursors and which process comprises: (a) contacting the feedstock with a hydrogenated recycle liquid containing dissolved hydrogen in a first hydrogenation reaction zone operated at hydrogenation conditions selected to minimize a hydrogen-rich gaseous phase and to selectively hydrogenate the feedstock comprising organic compounds and to produce a first hydrogenated stream comprising hydrocarbonaceous compounds and having a reduced tendency to produce polymers; (b) contacting at least a portion of the first hydrogenated stream with a hydrogen-rich gaseous stream in a saturation zone to produce a second hydrogenated stream containing dissolved hydrogen; (c) introducing at least a portion of the second hydrogenated stream containing dissolved hydrogen into the first hydrogenation reaction zone in step (a) as at least a portion of the hydrogenated recycle liquid; (d) contacting at least another portion of the second hydrogenated stream containing dissolved hydrogen with added hydrogen in a second hydrogenation reaction zone operated at hydrogenation conditions selected to produce a third hydrogenated stream comprising hydrogenated hydrocarbonaceous compounds and hydrogen; (e) separating the third hydrogenated stream in a separation zone to produce a hydrogen-rich gaseous stream and a fourth hydrogenated stream; and (f) recovering the hydrogen-rich gaseous stream and the fourth hydrogenated stream.

Yet another embodiment of the present invention may be characterized as a process for the hydroconversion of a feedstock comprising halogenated, diolefinic organic compounds which process comprises: (a) contacting the feedstock with a hydrogenated recycle liquid containing dissolved hydrogen in a first hydrogenation reaction zone operated at hydrogenation conditions selected to minimize a hydrogen-rich gaseous phase and to selectively hydrogenate halogenated, diolefinic organic compounds and to produce a first hydrogenated stream comprising hydrocarbonaceous compounds and having a reduced concentration of diolefinic compounds; (b) contacting at least a portion of the first hydrogenated stream with a hydrogen-rich gaseous stream in a saturation zone to produce a second hydrogenated stream containing dissolved hydrogen; (c) introducing at least a portion of the second hydrogenated stream containing dissolved hydrogen into the first hydrogenation reaction zone in step (a) as at least a portion of the hydrogenated recycle liquid; (d) contacting at least another portion of the second hydrogenated stream containing dissolved hydrogen with added hydrogen in a second hydrogenation reaction zone operated at hydrogenation conditions selected to produce a third hydrogenated stream comprising hydrogenated hydrocarbonaceous compounds and to generate at least one water-soluble hydrogen halide compound; (e) contacting the resulting effluent from the second hydrogenation zone comprising hydrogenated hydrocarbonaceous compounds, a hydrogen-rich gas and at least one water-soluble hydrogen halide compound with a halide-lean absorber solution in an absorption zone; (f) withdrawing a halide-rich absorber solution containing at least a portion of the water-soluble hydrogen halide compound from the absorption zone; (g) withdrawing a stream comprising hydrogenated hydrocarbonaceous compounds and a hydrogen-rich gas from the absorption zone; (h) introducing the stream from step (g) into a separation zone to produce a hydrogen-rich gaseous stream and a fourth hydrogenated stream comprising hydrocarbonaceous compounds and having a reduced concentration of halogenated organic compounds; and (i) recovering the fourth hydrogenated stream.

Other embodiments of the present invention encompass further such details such as preferred feedstocks, hydrogenation catalysts, absorber solutions, aqueous scrubbing solutions and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The present invention provides an improved integrated process for the hydroconversion of a feedstock comprising organic compounds which are polymer precursors. Although any feedstock containing organic compounds which are polymer precursors may be processed in one of the preferred embodiments of the present invention, for purposes of convenience the present invention is described in detail while referring to a feedstock containing halogenated diolefinic organic compounds. A wide variety of halogenated organic compounds are candidates for feed streams in accordance with one embodiment of the present invention. Examples of organic streams comprising halogenated, diolefinic organic compounds which are suitable for treatment by the process of the present invention are by-products from organic monomer and polymer production, hydrocarbonaceous pyrolysis effluents from thermal treatment plants, used lubricating oils, used solvents, halogenated hydrocarbonaceous by-products, oils contaminated with polychlorinated biphenyls (PCB), halogenated wastes, petrochemical by-products, by-products from chlorinated solvent production and other halogenated hydrocarbonaceous industrial wastes. It has been discovered that diolefinic halogenated organic compounds, for example, present a greater challenge for subsequent processing such as hydrogenation as compared with the saturated halogenated organic compounds. When diolefinic, halogenated organic compounds are present, they may readily be processed in the integrated hydrogenation process of the present invention. The diolefinic, halogenated organic feed streams which are contemplated for use in the present invention may also contain organic compounds which include sulfur, oxygen, nitrogen or metal components which may be simultaneously hydrogenated to remove or convert such components as desired. The diolefinic, halogenated organic compounds may also contain hydrogen and are therefore then referred to as hydrocarbonaceous compounds.

Preferred feedstocks containing diolefinic, halogenated organic compounds comprise a component selected from the group consisting of light by-products from the production of vinyl chloride monomer, fractionation column bottoms in the production of carbon tetrachloride, trichloroethylene and perchloroethylene, residues from the production of styrene, phenol, and cumene, used chlorinated solvents, chloroprene, epoxy containing streams, thermal or pyrolysis process effluents and mixed industrial waste liquors.

The diolefinic, halogenated organic compounds which are contemplated as feedstocks in the present invention preferably contain a halogen selected from the group consisting of chlorine, bromine and fluorine.

In accordance with one preferred embodiment of the present invention, a feedstock comprising diolefinic, halogenated organic compounds is introduced in admixture with a hydrogenated recycle liquid containing dissolved hydrogen into a catalytic hydrogenation zone containing hydrogenation catalyst and maintained at mild hydrogenation conditions selected to minimize a hydrogen-rich gaseous phase and to selectively hydrogenate halogenated, diolefinic organic compounds. This selective hydrogenation reduces the concentration of diolefinic compounds, for example, which possess the greatest tendency to form polymers and other high molecular weight compounds. This permits the feedstock to be further treated by hydrogenation without experiencing undesirable polymerization and the concomitant plugging of the process equipment. This catalytic hydrogenation zone may contain a fixed, ebullated or fluidized catalyst bed. This reaction zone is preferably maintained at mild conditions which are chosen to selectively saturate diolefinic halogenated organic compounds while simultaneously preventing the formation of polymers or higher molecular weight carbonaceous material. Preferred reaction zone conditions include an imposed pressure from about atmospheric (0 kPa gauge) to about 2,000 psig (13790 kPa gauge) and more preferably under a pressure from about 100 psig (689.5 kPa gauge) to about 1800 psig (12411 kPa gauge). Suitably, such reaction is conducted with a maximum catalyst bed temperature in the range of about 104° F. (40° C.) to about 650° F. (343° C.) selected to perform the desired saturation of diolefinic, halogenated organic compounds in order to reduce or eliminate the propensity of the diolefinic feed stream to form polymers and gum which are undesirable for further use or processing of the resulting hydrocarbonaceous stream. Although the primary function of this hydrogenation zone is used to saturate the diolefinic halogenated organic charge stream, it is also contemplated in accordance with the present invention that other desired hydrogenation conversion may also occur, such as dehalogenation, desulfurization, denitrification, oxygenate conversion and hydrocracking, for example. Further preferred operating conditions include liquid hourly space velocities in the range from about 0.05 hour$^{-1}$ to about 40 hr$^{-1}$ and combined feed ratios (defined as the sum of the fresh feed rate and the hydrogenated recycle liquid rate divided by the fresh feed rate) from about 0.1 to about 100 and more preferably from about 1 to about 10.

The resulting effluent from the first hydrogenation reaction zone which is used to selectively hydrogenate the halogenated, diolefinic organic feedstock is admixed with a hydrogen-rich gaseous stream to prepare a liquid containing dissolved hydrogen. The resulting liquid containing dissolved hydrogen is prepared in a saturator wherein the liquid is intimately contacted with a hydrogen-rich gas at operating conditions which preferably include a pressure which is essentially equal to the pressure maintained in the first hydrogenation reaction zone and at a temperature which prevents the boiling of the liquid. The amount of hydrogen-rich gas introduced into the saturator is not critical as long as a sufficient quantity is present to ensure the saturation of the liquid with hydrogen gas.

At least a portion of the liquid containing dissolved hydrogen is introduced into the first catalytic hydrogenation zone in admixture with the fresh feedstock as described above. At least another portion of the liquid containing dissolved hydrogen is introduced into a second catalytic hydrogenation zone containing hydrogenation catalyst and maintained at hydrogenation conditions. This second catalytic hydrogenation zone may contain a fixed, ebullated or fluidized catalyst bed. The second hydrogenation zone may contain one or more catalyst zones to aid in the temperature control of the highly exothermic hydrogenation reaction. The operating conditions selected for this catalytic hydrogenation zone are selected primarily to completely saturate and to dehalogenate the halogenated organic compounds which are introduced thereto and these operating conditions are generally more severe, i.e., promote greater hydrogenation than the operating conditions utilized in the first catalytic hydrogenation zone which conditions are selected to primarily hydrogenate diolefin compounds. This second catalytic hydrogenation zone is preferably maintained under an imposed pressure from about atmospheric (0 kPa gauge) to about 2000 psig (13790 kPa gauge) and more preferably under a pressure from about 100 psig (689.5 kPa gauge) to about 1800 psig (12411 kPa gauge). Suitably, such reaction is conducted with a maximum catalyst bed temperature in the range of about 122° F. (50° C.) to about 850° F. (454° C.) selected to perform the desired hydrogenation and dehalogenation conversion to significantly reduce the concentration of halogenated organic compounds contained in the combined feed stream. In accordance with the present invention, it is contemplated that the desired hydrogenation conversion includes, for example, dehalogenation, desulfurization, denitrification, olefin saturation, oxygenate conversion and hydrocracking. Further preferred operating conditions include liquid hourly space velocities in the range from about 0.05 hr.$^{-1}$ to about 20 hr.$^{-1}$ and hydrogen circulation rates from about 200 standard cubic feet per barrel (SCFB) (33.71 normal m$^3$/m$^3$) to about 100,000 SCFB (16851 normal m$^3$/m$^3$), preferably from about 200 SCFB (33.71 normal m$^3$/m$^3$) to about 50,000 SCFB (8427 normal m$^3$/m$^3$).

In the event that the temperature of the combined halogen-containing, organic feed stream which is introduced into the second hydrogenation reaction zone is not deemed to be exactly the temperature selected to operate the second catalytic hydrogenation zone, we contemplate that the temperature of the feed stream to be introduced into the hydrogenation zone may be adjusted either upward or downward in order to achieve the desired temperature in the catalytic hydrogenation zone. Such a temperature adjustment may be accomplished, for example, by either indirect heat exchange or by the addition of either cool or hot hydrogen.

In accordance with one embodiment of the present invention, the hydrocarbonaceous effluent containing at least one water-soluble hydrogen halide compound from the second hydrogenation zone is contacted with an absorber solution to recover the water-soluble hydrogen halide compound and to provide a hydrogenated hydrocarbonaceous liquid phase and a hydrogen-rich gaseous phase. The contact of the hydrocarbonaceous effluent from the second hydrogenation zone with the absorber solution may be performed in any convenient manner and in one embodiment is preferably conducted by a countercurrent contacting of the hydrocarbonaceous effluent with water or a lean aqueous scrubbing solution in an absorber or an absorption zone. An absorber solution rich in water-soluble hydrogen halide is then recovered from the absorber and may be used as recovered or may be regenerated to provide a lean absorber solution which may be recycled to the absorber to accept additional water-soluble hydrogen halide.

The absorber solution is preferably introduced into the absorber in an amount from about 1 to about 20 times the mass flow rate of the total feedstock charged to the second hydrogenation zone based on the composition of the effluent from the second hydrogenation zone. The absorber is preferably operated at conditions which include a temperature from about 32° F. (0° C.) to about 300° F. (149° C.) and a pressure from about atmospheric (0 kPa gauge) to about 2000 psig (13790 kPa gauge). The absorber is preferably operated at essentially the same pressure as the second hydrogenation zone subject to fluid flow pressure drop. The absorber solution is selected depending on the characteristics of the organic feed stream introduced into the second hydrogenation zone. In accordance with the present invention, at least some halogenated organic compounds are introduced as feedstock and therefore the absorber solution preferably contains water or a lean aqueous absorber solution containing a water-soluble hydrogen halide. In accordance with the present invention the hydrogen halide compound is recovered by dissolution in water or a lean aqueous solution of the hydrogen halide compound. This permits the subsequent recovery and use of a desirable and valuable hydrogen halide compound. The final selection of the absorber solution is dependent upon the particular hydrogen halide compounds which are present and the desired end product.

The resulting effluent from the absorber containing hydrogenated hydrocarbonaceous liquid phase and a hydrogen-rich gaseous phase is recovered and introduced into a vapor-liquid separator. The vapor-liquid separator is operated at conditions to provide a hydrogen-rich gaseous stream which is suitable for recycle and is preferably recycled together with fresh make-up hydrogen for further use in the process. A liquid hydrogenated hydrocarbonaceous stream is also recovered and removed from the vapor-liquid separator.

The preferred catalytic composites disposed within the hereinabove described hydrogenation zones can be characterized as containing a metallic component having hydrogenation activity, which component is combined with a suitable refractory carrier material of either synthetic or natural origin. The precise composition and method of manufacturing the carrier material is not considered essential to the present invention. Preferred carrier materials are alumina, silica, carbon and mixtures thereof. Suitable metallic components having hydrogenation activity are those selected from the group comprising the metals of Groups VI-B and VIII of the Periodic Table, as set forth in the *Periodic Table of the Elements*, E. H. Sargent and Company, 1964. Thus, the catalytic composites may comprise one or more metallic components from the group of molybdenum, tungsten, chromium, iron, cobalt, nickel, platinum, palladium, iridium, osmium, rhodium, ruthenium, and mixtures thereof. The concentration of the catalytically active metallic component, or components, is primarily dependent upon a particular metal as well as the physical and/or chemical characteristics of the particular organic feedstock. For example, the metallic components of Group VI-B are generally present in an amount within the range of from about 1 to about 20 weight percent, the iron-group metals in an amount within the range of about 0.2 to about 10 weight percent, whereas the noble metals of Group VIII are preferably present in an amount within the range of from about 0.1 to about 5 weight percent, all of which are calculated as if these components existed within the catalytic composite in the elemental state. It is further contemplated that hydrogenation catalytic composites may comprise one or more of the following components: cesium, francium, lithium, potassium, rubidium, sodium, copper, gold, silver, cadmium, mercury and zinc. Preferred hydrogenation catalysts comprise alumina and palladium.

The resulting hydrogenated hydrocarbonaceous liquid phase which preferably comprises less than about 0.1% of the halogenated organic compounds processed is in one embodiment of the present invention recovered from the hydrogen-rich gaseous phase in a separation zone as described hereinabove which is maintained at essentially the same pressure as the absorption zone and, as a consequence, contains dissolved hydrogen and low molecular weight normally gaseous hydrocarbons if present. In accordance with one embodiment of the present invention, it is preferred that the hydrogenated hydrocarbonaceous liquid phase comprising the hereinabove mentioned gases be stabilized in a convenient manner, such as, for example, by stripping or flashing to remove the normally gaseous components to provide a stable hydrogenated distillable hydrocarbonaceous product. In some cases, we contemplate that a significant portion of the hydrogenated hydrocarbonaceous product may comprise methane, ethane, propane, butane, hexane and admixtures thereof. An adsorbent/stripper arrangement may conveniently be used to recover methane and ethane. Fractionation may conveniently be used to produce purified product streams such as liquid propane or LPG containing propane and butane.

In the drawing, the process of the present invention is illustrated by means of a simplified flow diagram in which such details as total number of reaction zone vessels, pumps, instrumentation, heat-exchange and heat-recovery circuits, compressors and similar hardware have been deleted as being non-essential to an understanding of the techniques involved. The use of such miscellaneous appurtenances are well within the purview of one skilled in the art.

With reference now to the drawing, a diolefinic halogenated organic feed stream comprising halogenated organic compounds is introduced into the process via conduit 1 and is contacted with a hydrogenated recycle liquid containing dissolved hydrogen which is provided via conduit 8 and is hereinafter described. The diolefinic, halogenated organic feed stream comprising halogenated organic compounds and the hydrogenated recycle liquid containing dissolved hydrogen are introduced into hydrogenation reaction zone 2 via conduit 1. The resulting hydrogenated organic stream having a reduced concentration of diolefinic compounds is removed from hydrogenation reaction zone 2 via conduit 3, is admixed with a hydrogen-rich gaseous recycle stream provided by conduit 18 and introduced into saturator 4 which is operated at a temperature and pressure sufficient to dissolve the required hydrogen. A portion of the hydrogenated liquid containing dissolved hydrogen gas is removed from saturator 4 via conduit 6, pump 7 and conduit 8 to provide the hydrogenated recycle liquid previously mentioned. Another portion of the hydrogenated liquid containing dissolved hydrogen is removed from saturator 4 via conduit 6, pump 7, conduit 9 and conduit 5, and introduced into hydrogenation zone 10. A hydrogen-rich gaseous stream is removed from saturator 4 via conduit 5 and introduced into hydrogenation zone 10. A hydrogen-rich gaseous recycle stream provided by conduit 18 and 5 is also introduced into hydrogenation zone 10. The resulting hydrogenated hydrocarbonaceous stream is removed from hydrogenation reaction zone 10 via conduit 11, is cooled in heat exchanger 12 and introduced into absorber 13 via conduit 11. The hydrocarbonaceous stream is contacted in a countercurrent flow with a halide-lean absorber solution which is introduced via conduit 14. A halide-rich absorber solution is removed from absorber 13 via conduit 15. A resulting steam containing hydrogenated hydrocarbonaceous compounds is removed from absorber 13 via conduit 16 and introduced into high pressure vapor-liquid separator 17. A hydrogen-rich gaseous stream is removed from high pressure vapor-liquid separator 17 via conduit 18 and recycled as described hereinabove. Since hydrogen is lost in the process by means of a portion of the hydrogen being dissolved in the exiting liquid hydrocarbon and hydrogen being consumed during the hydrogenation reaction, it is necessary to supplement the hydrogen-rich gaseous stream with make-up hydrogen from some suitable external source, for example, a catalytic reforming unit or a hydrogen plant. Make-up hydrogen may be introduced into the system at any convenient and suitable point, and is introduced in the drawing via conduit 19. A liquid hydrogenated hydrocarbonaceous stream comprising hydrogen in solution is removed from high pressure vapor-liquid separator 17 via conduit 21 and is introduced into low pressure vapor-liquid separator 22. A gaseous stream comprising hydrogen and any normally gaseous hydrocarbons present is removed from low pressure vapor-liquid separator 22 via conduit 23 and recovered. A normally liquid distillable hydrogenated hydrocarbonaceous product is removed from low pressure vapor-liquid separator 22 via conduit 24 and recovered. In the event that the liquid distillable hydrogenated hydrocarbonaceous product removed via conduit 24 is propane, for example, and is therefore not accurately described as normally liquid, the low pressure vapor-liquid separator 22 may be necessarily operated at a pressure in the range from about 300 psig (2068 kPa gauge) to about 500 psig (3447 kPa gauge).

The process of the present invention is further demonstrated by the following illustrative embodiment. This illustrative embodiment is however not presented to unduly limit the process of this invention, but to further illustrate the advantages of the hereinabove described embodiments. The following data were not completely obtained by the actual performance of the present invention, but were derived from pilot plant data and are considered prospective and reasonably illustrative of the expected performance of the invention.

ILLUSTRATIVE EMBODIMENT

A diolefinic, halogenated organic feedstock having the characteristics presented in Table 1 is charged at a rate of 100 mass units per hour to a first hydrogenation zone together with a hydrogenated recycle liquid containing 0.3 mass units of dissolved hydrogen in an amount of 1400 mass units per hour (a corresponding combined feed ratio of 15).

TABLE 1

| Diolefinic, Halogenated Organic Feedstock Properties | |
|---|---|
| Specific Gravity @60° F. (15° C.) | 1.37 |
| Distillation, °C. | |
| IBP | 0 |
| 5 | 55 |
| 10 | 65 |
| 50 | 84 |
| 90 | 130 |
| 95 | 150 |
| EP | 200 |
| % Over | 99 |
| % Residue | 1 |
| Composition, Weight Percent | |
| Chloroprene | 6 |
| Chlorinated Olefins | 15 |
| Chlorinated Saturates | 78 |
| Chlorinated Aromatics | 1 |

An analysis of the combined feed is presented in Table 2.

TABLE 2

| Combined Feed to the First Hydrogenation Zone | |
|---|---|
| Composition, Weight Percent | |
| Chloroprene | 0.4 |
| Chlorinated Olefins | 20.6 |
| Chlorinated Saturates | 78.0 |
| Chlorinated Aromatics | 1.0 |
| Dissolved Hydrogen | <0.01 |

The first hydrogenation zone contains a palladium hydrogenation catalyst and is operated at conditions which include a pressure of 955 psig, a temperature of 185° F. and a liquid hourly space velocity of 2 $hr^{-1}$. The chloroprene component (1,3 dichloro butadiene) of the feedstock is selectively hydrogenated in a substantially liquid phase reaction.

The resulting effluent from the first hydrogenation zone is contacted with a hydrogen-rich gaseous stream to saturate the liquid with dissolved hydrogen and then is split into two portions, the first of which is used as the hereinabove described hydrogenated recycle liquid and the second portion (~100 mass units) of which is admixed with a hydrogen rich recycle gas stream and introduced into a second hydrogenation zone.

The second hydrogenation zone is operated to dechlorinate the feedstock and to concomitantly produce hydrogen chloride with a palladium promoted catalyst at conditions which include a pressure of 945 psig, an outlet temperature of 550° F. and liquid hourly space velocity of 0.15 hr$^{-1}$. The resulting effluent from the second hydrogenation zone (see Table 3) is in the vapor phase and is introduced into a hydrogen chloride absorption zone wherein the vapor phase is contacted with a halogen-lean absorber solution to remove and recover the hydrogen chloride in an amount of about 73 mass units.

TABLE 3

| Second Hydrogenation Zone Effluent Vapor Composition, Weight Percent | |
|---|---|
| Hydrogen Chloride | 58.8 |
| Hydrocarbon | 20.4 |
| Chlorinated Saturate | 0.8 |
| Hydrogen | 20 |

The hydrogen chloride absorber is operated at 900 psig and 200° F., and is greater than 99% efficient in the removal of hydrogen chloride. The resulting vapor leaving the hydrogen chloride absorber is chilled and the hydrocarbons are partially condensed in a high pressure separator. A hydrogen-rich gaseous phase is removed from the high pressure separator and recycled. The net hydrocarbon liquid is removed from the high pressure separator and introduced into a separation zone wherein the liquid hydrocarbon is further recovered from elemental hydrogen gas.

The foregoing description, drawing and illustrative embodiment clearly illustrate the advantages encompassed by the process of the present invention and the benefits to be afforded with the use thereof.

What is claimed:

1. A process for the hydroconversion of a feedstock comprising organic compounds which are polymer precursors and which process comprises:
    (a) contacting said feedstock with a hydrogenated recycle liquid containing dissolved hydrogen in a first hydrogenation reaction zone operated at hydrogenation conditions selected to minimize a hydrogen-rich gaseous phase and to selectively hydrogenate said feedstock comprising organic compounds and to produce a first hydrogenated stream comprising hydrocarbonaceous compounds and having a reduced tendency to produce polymers;
    (b) contacting at least a portion of said first hydrogenated stream with a hydrogen-rich gaseous stream in a saturation zone to produce a second hydrogenated stream containing dissolved hydrogen;
    (c) introducing at least a portion of said second hydrogenated stream containing dissolved hydrogen into said first hydrogenation reaction zone in step (a) as at least a portion of said hydrogenation recycle liquid;
    (d) contacting at least another portion of said second hydrogenated stream containing dissolved hydrogen with added hydrogen in a second hydrogenation reaction zone operated at hydrogenation conditions selected to produce a third hydrogenated stream comprising hydrogenated hydrocarbonaceous compounds and hydrogen; and
    (e) recovering said third hydrogenated stream.

2. The process of claim 1 wherein said feedstock comprising organic compounds which are polymer precursors comprises a component selected from the group consisting of halogenated-diolefinic organic compounds of vinyl chloride monomer, fractionation column bottoms in the production of carbon tetrachloride, trichloroethylene and perchloroethylene, residues from the production of styrene, phenol and cumene, used chlorinated solvents, chloroprene, epoxy containing streams, thermal process effluents, pyrolysis process effluents and mixed industrial wastes.

3. The process of claim 1 wherein said second hydrogenation reaction zone comprises at least two catalyst zones.

4. The process of claim 1 wherein said first hydrogenation reaction zone is operated at conditions which include a pressure from about atmospheric (0 kPa gauge) to about 2000 psig (13790 kPa gauge), and a maximum catalyst temperature from about 104° F. (40° C.) to about 850° F. (454° C.).

5. The process of claim 1 wherein said second hydrogenation reaction zone is operated at conditions which include a pressure from about atmospheric (0 kPa gauge) to about 2000 psig (13790 kPa gauge), a maximum catalyst temperature from about 122° F. (50° C.) to about 850° F. (454° C.) and a hydrogen circulation rate from about 200 SCFB (33.7 normal m$^3$/m$^3$) to about 50,000 SCFB (8427 normal m$^3$/m$^3$).

6. The process of claim 1 wherein said feedstock comprising organic compounds which are polymer precursors contains a halogen selected from the group consisting of chlorine, bromine and fluorine.

7. The process of claim 1 wherein said saturation zone in step (b) is at a pressure essentially equal to the pressure maintained in said first hydrogenation reaction zone.

8. The process of claim 1 wherein said first hydrogenation zone contains a hydrogenation catalyst which comprises alumina and palladium.

9. The process of claim 1 wherein said second hydrogenation zone contains a hydrogenation catalyst which comprises alumina and palladium.

10. A process for the hydroconversion of a feedstock comprising organic compounds which are polymer precursors and which process comprises:
    (a) contacting said feedstock with a hydrogenated recycle liquid containing dissolved hydrogen in a first hydrogenation reaction zone operated at hydrogenation conditions selected to minimize a hydrogen-rich gaseous phase and to selectively hydrogenate said feedstock comprising organic compounds and to produce a first hydrogenated stream comprising hydrocarbonaceous compounds and having a reduced tendency to produce polymers;
    (b) contacting at least a portion of said first hydrogenated stream with a hydrogen-rich gaseous stream in a saturation zone to produce a second hydrogenated stream containing dissolved hydrogen;
    (c) introducing at least a portion of said second hydrogenated stream containing dissolved hydrogen into said first hydrogenation reaction zone in step (a) as at least a portion of said hydrogenated recycle liquid;
    (d) contacting at least another portion of said second hydrogenated stream containing dissolved hydrogen with added hydrogen in a second hydrogenation reaction zone operated at hydrogenation conditions selected to produce a third hydrogenated stream comprising hydrogenated hydrocarbonaceous compounds and hydrogen;

(e) separating said third hydrogenated stream in a separation zone to produce a hydrogen-rich gaseous stream and a fourth hydrogenated stream; and (f) recovering said hydrogen-rich gaseous stream and said fourth hydrogenated stream.

11. The process of claim 10 wherein at least a portion of said hydrogen-rich gaseous stream recovered in step (e) is recycled to step (b).

12. The process of claim 10 wherein said feedstock comprising organic compounds which are polymer precursors comprises a component selected from the group consisting of halogenateddiolefinic organic compounds of vinyl chloride monomer, fractionation column bottoms in the production of trichloroethylene and perchloroethylene, residues from the production of styrene, phenol and cumene, used chlorinated solvents, chlorophene, epoxy containing streams and mixed industrial waste liquors.

13. The process of claim 10 wherein said second hydrogenation reaction zone comprises at least two catalyst zones.

14. The process of claim 10 wherein said first hydrogenation reaction zone is operated at conditions which include a pressure from about atmospheric (0 kPa gauge) to about 2000 psig (13790 kPa gauge), and a maximum catalyst temperature from about 104° F. (40° C.) to about 850° F. (454° C.).

15. The process of claim 10 wherein said second hydrogenation reaction zone is operated at conditions which include a pressure from about atmospheric (0 kPa gauge) to about 2000 psig (13790 kPa gauge), a maximum catalyst temperature from about 122° F. (50° C.) to about 850° F. (454° C.) and a hydrogen circulation rate from about 200 SCFB (33.7 normal m$^3$/m$^3$) to about 50,000 SCFB (8427 normal m$^3$/m$^3$).

16. The process of claim 10 wherein said feedstock comprising organic compounds which are polymer precursors contains a halogen selected from the group consisting of chlorine, bromine and fluorine.

17. The process of claim 10 wherein said saturation zone in step (b) is conducted at a pressure essentially equal to the pressure maintained in said first hydrogenation reaction zone.

18. The process of claim 10 wherein said first hydrogenation zone contains a hydrogenation catalyst which comprises alumina and palladium.

19. The process of claim 10 wherein said second hydrogenation zone contains a hydrogenation catalyst which comprises alumina and palladium.

20. A process for the hydroconversion of a feedstock comprising halogenated, diolefinic organic compounds which process comprises:

(a) contacting said feedstock with a hydrogenated recycle liquid containing dissolved hydrogen in a first hydrogenation reaction zone operated at hydrogenation conditions selected to minimize a hydrogen-rich gaseous phase and to selectively hydrogenate halogenated, diolefinic organic compounds and to produce a first hydrogenated stream comprising hydrocarbonaceous compounds and having a reduced concentration of diolefinic compounds;

(b) contacting at least a portion of said first hydrogenated stream with a hydrogen-rich gaseous stream in a saturation zone to produce a second hydrogenated stream containing dissolved hydrogen;

(c) introducing at least a portion of said second hydrogenated stream containing dissolved hydrogen into said first hydrogenation reaction zone in step (a) as at least a portion of said hydrogenated recycle liquid;

(d) contacting at least another portion of said second hydrogenated stream containing dissolved hydrogen with added hydrogen in a second hydrogenation reaction zone operated at hydrogenation conditions selected to produce a third hydrogenated stream comprising hydrogenated hydrocarbonaceous compounds and to generate at least one water-soluble hydrogen halide compound;

(e) contacting the resulting effluent from said second hydrogenation zone comprising hydrogenated hydrocarbonaceous compounds, a hydrogen-rich gas and at least one water-soluble hydrogen halide compound with a halide-lean absorber solution in an absorption zone;

(f) withdrawing a halide-rich absorber solution containing at least a portion of said water-soluble hydrogen halide compound from said absorption zone;

(g) withdrawing a stream comprising hydrogenated hydrocarbonaceous compounds and a hydrogen-rich gas from said absorption zone;

(h) introducing said stream from step (g) into a separation zone to produce a hydrogen-rich gaseous stream and a fourth hydrogenated stream comprising hydrocarbonaceous compounds and having a reduced concentration of halogenated organic compounds; and (i) recovering said fourth hydrogenated stream.

21. The process of claim 20 wherein at least a portion of said hydrogen-rich gaseous stream recovered in step (h) is recycled to step (b).

22. The process of claim 20 wherein said feedstock comprising halogenated, diolefinic organic compounds comprises a component selected from the group consisting of light by-products from the production of vinyl chloride monomer, fractionation column bottoms in the production of trichloroethylene and perchloroethylene, residues from the production of styrene, phenol and cumene, used chlorinated solvents, chlorophrene, epoxy containing streams and mixed industrial waste liquors.

23. The process of claim 20 wherein said second hydrogenation reaction zone comprises at least two catalyst zones.

24. The process of claim 20 wherein said first hydrogenation reaction zone is operated at conditions which include a pressure from about atmospheric (0 kPa gauge) to about 2000 psig (13790 kPa gauge), and a maximum catalyst temperature from about 104° F. (40° C.) to about 850° F. (454° C.).

25. The process of claim 20 wherein said second hydrogenation reaction zone is operated at conditions which include a pressure from about atmospheric (0 kPa gauge) to about 2000 psig (13790 kPa gauge), a maximum catalyst temperature from about 122° F. (50° C.) to about 850° F. (454° C.) and a hydrogen circulation rate from about 200 SCFB (33.7 normal m$^3$/m$^3$) to about 50,000 SCFB (8427 normal m$^3$/m$^3$).

26. The process of claim 20 wherein said feedstock comprising halogenated diolefinic organic compounds contains a halogen selected from the group consisting of chlorine, bromine and fluorine.

27. The process of claim 20 wherein said saturation zone in step (b) is conducted at a pressure essentially equal to the pressure maintained in said first hydrogenation reaction zone.

28. The process of claim 20 wherein said water-soluble hydrogen halide compound is selected from the group consisting of hydrogen chloride and hydrogen fluoride.

29. The process of claim 20 wherein said absorption zone is operated at conditions which include a temperature from about 32° F. (0° C.) to about 300° F. (149° C.) and a pressure from about atmospheric (0 kPa gauge) to about 2000 psig (13790 kPa gauge).

30. The process of claim 20 wherein said absorption zone is operated at essentially the same pressure as said second hydrogenation zone.

31. The process of claim 20 wherein said halide-lean absorber solution is introduced into said absorption zone in an amount from about 1 to about 20 times the mass flow rate of the total feedstock charged to the second hydrogenation zone.

32. The process of claim 20 wherein said first hydrogenation zone contains a hydrogenation catalyst which comprises alumina and palladium.

33. The process of claim 20 wherein said second hydrogenation zone contains a hydrogenation catalyst which comprises alumina and palladium.

* * * * *